United States Patent [19]

Hoshino et al.

[11] Patent Number: 5,776,742
[45] Date of Patent: Jul. 7, 1998

[54] ALDEHYDE DEHYDROGENASE ENZYME

[75] Inventors: Tatsuo Hoshino, Kamakura; Teruhide Sugisawa, Yokohama, both of Japan

[73] Assignee: Roche Vitamins Inc., Parsippany, N.J.

[21] Appl. No.: 796,125

[22] Filed: Feb. 6, 1997

[30] Foreign Application Priority Data

Feb. 19, 1996 [EP] European Pat. Off. ............ 96102440

[51] Int. Cl.⁶ ..................................................... C12P 7/60
[52] U.S. Cl. ...................... 435/138; 435/136; 435/190; 435/252.1; 435/822
[58] Field of Search ................................ 435/136, 138, 435/190, 252.1, 822

[56] References Cited

U.S. PATENT DOCUMENTS 3,907,639  9/1975  Makover et al.
5,437,989  8/1995  Asakura et al. ........................ 435/190

OTHER PUBLICATIONS

Hoshino, T., et al., *Agric. Biol. Chem.*, 55(3):665–670 (1991).
Kitamura, I., et al., *Eur. J. Appl. Microbiol.*, 2:1–7 (1975).
Makover, S., et al., *Biotechnol. Bioeng.*, 17:1485–1514 (1975).

*Primary Examiner*—Herbert J. Lilling
*Attorney, Agent, or Firm*—George W. Johnston; Dennis P. Tramaloni; Joseph P. Kirk, Jr.

[57] ABSTRACT

An aldehyde dehydrogenase having the physico-chemical properties: molecular weight: 91,000±5,000; substrate specificity:active on aldehyde compounds; inhibition: by $Cu^{2+}$, $Zn^{2+}$, $Ni^{2+}$ and ethylenediamine tetraacetic acid; optimum pH: 6.0–8.5; optimum temperature: 20°–40° C.; and stimulator: $Ca^{2+}$ and pyrroloquinoline quinone, is derived from a microorganism belonging to the genus Gluconobacter. Said aldehyde dehydrogenase can be produced by cultivating a microorganism of the genus Gluconobacter which is capable of producing an aldehyde dehydrogenase having the above properties, in an aqueous nutrient medium under aerobic conditions, disrupting the cells of the microorganism and isolating and purifying the aldehyde dehydrogenase from the cell-free extract of the disrupted cells of the microorganism. The aldehyde dehydrogenase is useful for the preparation of 2-keto-L-gulonic acid (2-KGA) which can be produced from L-sorbosone by contacting L-sorbosone with (i) the aldehyde dehydrogenase in the presence of an electron acceptor, (ii) a Gluconobacter microorganism capable of producing the aldehyde dehydrogenase in an aqueous medium under aerobic conditions or (iii) a cell-free extract of said microorganism, and in each case isolating the resulting 2-keto-L-gulonic acid from the reaction mixture.

14 Claims, No Drawings

ALDEHYDE DEHYDROGENASE ENZYME

BRIEF SUMMARY OF THE INVENTION

The invention relates to an enzyme, namely aldehyde dehydrogenase (ADH), a process for producing the same and a process for producing 2-keto-L-gulonic acid (2-KGA) from L-sorbosone utilizing said enzyme. 2-Keto-L-gulonic acid is an important intermediate for the production of vitamin C.

BACKGROUND OF THE INVENTION

The reaction to convert L-sorbosone to 2-keto-L-gulonic acid using microorganisms is known. In U.S. Pat. No. 3,907,639, the microorganisms belonging to the genus Acetobacter, Pseudomonas, Escherichia, Serratia, Bacillus, Staphylococcus, Aerobacter, Alcaligenes, Penicillium, Candida and Gluconobacter are reported to be capable of promoting this reaction. Furthermore, Kitamura et al. (Eur. J. Appl. Microbiol., 2, 1, 1975) report that the enzyme found in *Gluconobacter melanogenus* IFO 3293 and which oxidizes L-sorbosone requires neither a coenzyme nor an electron acceptor for the development of enzyme activity. Makover et al. (Biotechnol. Bioeng. 17, 1485, 1975) report the presence of L-sorbosone dehydrogenase activity in the particulate fraction of *Pseudomonas putida* ATCC 21812 and of *Gluconobacter melanogenus* IFO 3293. They also indicate that nicotine amide adenine dinucleotide (NAD) or nicotine amide adenine dinucleotide phosphate (NADP) does not act as a coenzyme for the enzyme. Hoshino et al. [Agric. Biol. Chem., 55, 665 (1991)] purified and characterized the enzyme which catalyzes the oxidation of L-sorbosone to 2-keto-L-gulonic acid in the presence of nicotine amide adenine dinucleotide or nicotine amide adenine dinucleotide phosphate.

In the context of the present invention, microorganisms belonging to the genus Gluconobacter have been studied more closely and, as a result it has been found that another aldehyde dehydrogenase enzyme which catalyzes the oxidation of L-sorbosone to 2-keto-L-gulonic acid can be obtained from said microorganisms. Furthermore, it has been found that the aldehyde dehydrogenase provided by the present invention oxidizes L-sorbosone to 2-keto-L-gulonic acid in the presence of electron acceptors, such as, 2,6-dichlorophenolindophenol (DCIP), phenazine methosulfate (PMS), ferricyanide or cytochrome c, but that nicotine amide adenine dinucleotide, nicotine amide adenine dinucleotide phosphate and oxygen are not suitable as electron acceptors. Thus, aldehyde dehydrogenase is clearly distinct from the known L-sorbosone dehydrogenase.

An object of the present invention is to provide an aldehyde dehydrogenase enzyme which acts on L-sorbosone to produce 2-keto-L-gulonic acid and which has the following physico-chemical properties:

a) Molecular weight: 91,000±5,000 (consisting of two homologous subunits, each having a molecular weight of 44,000±2,000)
b) Substrate specificity: active on aldehyde compounds
c) Inhibition: by $Cu^{2+}$, $Zn^{2+}$, $Ni^{2+}$ and ethylenediamine tetraacetic acid (EDTA)
d) Optimum pH: 6.0–8.5
e) Optimum temperature: 20°–40° C.
f) Stimulator: $Ca^{2+}$ and pyrroloquinoline quinone (PQQ).

Another object of the present invention is to provide a process for producing the aldehyde dehydrogenase of the invention, as defined above, by: cultivating a microorganism belonging to the genus Gluconobacter, which is capable of producing the aldehyde dehydrogenase having the above properties, in an aqueous nutrient medium under aerobic conditions; disrupting the cells of the microorganism; and isolating and purifying the aldehyde dehydrogenase from the cell-free extract of the disrupted cells of the microorganism. Yet another object of the present invention is to provide a process for producing 2-keto-L-gulonic acid from L-sorbosone utilizing the aldehyde dehydrogenase of the invention, which process comprises contacting L-sorbosone with (i) an aldehyde dehydrogenase, as defined above, in the presence of an electron acceptor, or (ii) a microorganism belonging to the genus Gluconobacter which is capable of producing the aldehyde dehydrogenase, as defined above, in an aqueous nutrient medium under aerobic conditions, or (iii) a cell-free extract of said microorganism, and in each of the cases (i), (ii) and (iii) isolating the resulting 2-keto-L-gulonic acid from the reaction mixture.

The physico-chemical properties of the purified sample of the aldehyde dehydrogenase, prepared according to the Examples mentioned hereinafter, are as follows:

1) Enzyme activity

The aldehyde dehydrogenase of the present invention catalyzes the oxidation of L-sorbosone to 2-keto-L-gulonic acid in the presence of an electron acceptor according to the following reaction formula:

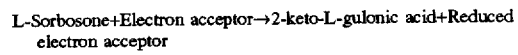
L-Sorbosone+Electron acceptor→2-keto-L-gulonic acid+Reduced electron acceptor The enzyme does not work with oxygen as an electron acceptor. This was affirmed by the failure of the enzyme to convert L-sorbosone to 2-keto-L-gulonic acid using oxygen as a possible electron acceptor. Furthermore, no oxygen consumption was detected in the reaction mixture as detected with a dissolved oxygen probe. However, any conventional compound which has the ability to act as an electron acceptor can be utilized in conjunction with the enzyme of this invention. As an electron acceptor, 2,6-dichlorophenolindophenol, phenazine methosulfate, ferricyanide or cytochrome c is preferred.

The enzyme assay was performed as follows:

The basal reaction mixture for assaying aldehyde dehydrogenase activity consisted of 0.1 mM 2,6-dichlorophenolindophenol, 1.0 mM phenazine methosulfate, 50 mM potassium phosphate buffer (pH 7.0), 2.0 mM L-sorbosone, enzyme solution and water in a final volume of 0.5 ml, which was prepared just before the assay. The reaction was started at 25° C. with L-sorbosone and the enzyme activity was measured as the initial reduction rate of 2,6-dichlorophenolindophenol at 600 nm. One unit of the enzyme activity was defined as the amount of the enzyme which catalyzed the reduction of 1 gmole of 2,6-dichlorophenolindophenol per minute. The extinction coefficient of 2,6-dichlorophenolindophenol at pH 7.0 was taken as 14.5 $mM^{-1}$. A reference cuvette contained all of the above except for L-sorbosone.

The protein concentration was measured with the BCA protein assay reagent (Pierce, Rockford, Ill.).

2) Substrate specificity

Substrate specificity of the enzyme was determined using the same enzyme assay method as described under 1) above, except that various substrate solutions (100 mM) were used instead of L-sorbosone. Substrate specificities of the purified enzyme for various substrates were investigated (cf. Table 1).

TABLE 1

| Substrate specificity of the ADH | |
|---|---|
| Substrate | Relative activity (%) |
| L-Sorbosone | 100 |
| L-Sorbose | 0 |
| D-Sorbitol | 0 |
| n-Propanol | 0 |
| iso-Propanol | 0 |
| D-Ribose | 33.3 |
| D,L-Glyceraldehyde | 788.9 |
| D-Glucosone | 77.8 |
| D-Mannose | 62.2 |
| D-Fructose | 0 |
| D-Glucose | 188.9 |

The relative activity of the aldehyde dehydrogenase from *Gluconobacter oxydans* DSM 4025 (FERM BP-3812) for D,L-glyceraldehyde and D-glucose was about 8 and, respectively, 2 times higher than that for L-sorbosone.

3) Optimum pH

The correlation between the reaction rate of the aldehyde dehydrogenase and pH values of the reaction mixture was determined using the same enzyme assay method as described under 1) above, except that various pHs and buffers were used (cf. Table 2).

TABLE 2

Optimum pH for the ADH activity

| | Relative activity (%)[a] Buffers | | |
|---|---|---|---|
| pH value | 0.1 M McIlvain | 0.1 M Potassium phosphate | 0.2 M Tris-HCl |
| 4.0 | — | — | — |
| 4.5 | — | — | — |
| 5.0 | — | — | — |
| 5.5 | 69.7 | — | — |
| 6.0 | 72.6 | 70.0 | — |
| 6.5 | — | 93.5 | — |
| 7.0 | 79.0 | 87.1 | 93.5 |
| 7.5 | — | 90.3 | — |
| 8.0 | 63.9 | — | 100 |
| 8.5 | — | — | 88.7 |
| 9.0 | — | — | 78.4 | a) Data are expressed as a percentage of the activity at pH 8.0 of Tris-HCl buffer.

4) pH stability

The enzyme was kept standing in buffers of various pHs for 6 days at 0° C., and then the residual activity was measured using the same enzyme assay method as described under 1) above. The results of the measurement are shown in Table 3. The purified enzyme was relatively stable at a pH around 7.5.

TABLE 3 pH Stability for the ADH activity

| | Relative activity (%)[a] Buffers | | |
|---|---|---|---|
| pH value | 0.1 M McIlvain | 0.1 M Potassium phosphate | 0.2 M Tris-HCl |
| 5.5 | 0.46 | — | — |
| 6.0 | 2.74 | 3.90 | — |
| 6.5 | 8.45 | 15.8 | — |
| 7.0 | 24.0 | 52.5 | 77.2 |
| 7.5 | 60.5 | 100 | 94.3 |
| 8.0 | 97.0 | — | 70.8 |
| 8.5 | — | — | 47.9 |
| 9.0 | — | — | 35.5 | a) Data are expressed as a percentage of the activity at pH 7.5 of 0.1M potassium phosphate buffer.

5) Thermostability

Thermostability of the enzyme was tested by incubating it for 5 minutes at various temperatures in 50 mM potassium phosphate buffer (pH 7.5), and then the treated enzyme was cooled down immediately in ice water. Residual activity was measured using the same enzyme assay method as described under 1) above. The enzyme was stable up to 35° C., and lost about 50 and 60% of its activity after it had been incubated at 40° and 45° C., respectively (cf. Table 4, column A).

TABLE 4

Effects of temperature on the stability and the activity of ADH

| Temperature | Relative activity (%) | |
|---|---|---|
| (°C.) | (A) | (B) |
| 0 | 100 | —* |
| 20 | — | 96.4 |
| 25 | 100 | 100 |
| 30 | 100 | 80.0 |
| 35 | 100 | 73.9 |
| 40 | 54.1 | 15.2 |
| 45 | 38.8 | 16.4 |
| 50 | 10.4 | — |
| 55 | 4.0 | — |
| 60 | 2.4 | — |

*not tested.

(A) Enzyme stability test (B) Test for optimal temperature evaluation

Data are expressed as a percentage of the activity at 25° C.

6) Optimum temperature

The enzyme activities were measured at temperatures from 20° to 45° C. The optimum temperature of the enzyme was 25° C. (cf. Table 4, column B).

7) Effects of metal ions, enzyme inhibitors and pyrroloquinoline quinone on the activity of aldehyde dehydrogenase The effects of metal ions, enzyme inhibitors and pyrroloquinoline quinone on the activity of the aldehyde dehydrogenase were examined by measuring the activity using the same assay method as described under 1) above. Each compound solution was stirred into the basal reaction mixture and the reaction was started with the addition of the enzyme (cf. Tables 5 and 6).

TABLE 5

Effects of various metals on the activity of ADH

| Metal | Concentration (mM) | Relative activity (%) |
|---|---|---|
| None | — | 100 |
| $Ca(NO_3)_2 \cdot 4H_2O$ | 0.0387 | 294 |
|  | 0.19 | 450 |
| $CaCl_2$ | 0.0387 | 337 |
| $CuCl_2 \cdot 6H_2O$ | 0.0387 | 100 |
|  | 0.19 | 50 |
|  | 0.374 | 0 |
| $CuSO_4 \cdot 7H_2O$ | 0.19 | 100 |
|  | 0.374 | 61.9 |
| $Fe_2(SO_4)_3 \cdot nH_2O$ | 0.0387 | 100 |
|  | 0.228 | 64.0 |
|  | 0.374 | 44.9 |
|  | 0.41 | 30.4 |
| $MgSO_4 \cdot 7H_2O$ | 0.19 | 79.3 |
|  | 0.374 | 39.9 |
| $Na_2MoO_4 \cdot 2H_2O$ | 0.19 | 69.7 |
|  | 0.374 | 42.1 |
| $TiCl_4$ | 0.19 | 100 |
|  | 0.374 | 80 |
| $ZnCl_2$ | 0.19 | 36.1 |
|  | 0.374 | 21.1 |
| $ZnSO_4 \cdot 7H_2O$ | 0.374 | 32.6 |
| $NiSO_4 \cdot 6H_2O$ | 0.375 | 17.6 |

As shown in Table 5, enzyme reaction was strongly stimulated by about 3- to 4.5-fold in the presence of 0.04 to 0.2 mM $Ca^{2+}$, whereas $Cu^{2+}$, $Fe^{3+}$, $Mg^{2+}$, $Mo^{6+}$, $Ti^{4+}$, $Zn^{2+}$ and $Ni^{2+}$ inhibited the enzyme activity.

TABLE 6

Effects of enzyme inhibitors and PQQ on the activity of ADH

| Compound | Concentration (mM) | Relative activity (%) |
|---|---|---|
| None | — | 100 |
| EDTA | 0.194 | 3.8 |
|  | 0.480 | 2.6 |
|  | 0.980 | 1.6 |
| Quinine | 0.950 | 117.6 |
|  | 1.870 | 111.8 |
| N-Ethylmaleimide | 0.950 | 94.1 |
|  | 1.870 | 76.5 |
| Sodium azide | 0.950 | 104.8 |
|  | 1.870 | 95.2 |
| Monoiodoacetate | 0.950 | 93.7 |
|  | 1.870 | 87.3 |
| $Na_2HAsO_4 \cdot 7H_2O$ | 0.950 | 100 |
|  | 1.870 | 107.1 |
| Sodium fluoroacetate | 0.950 | 118.2 |
|  | 1.870 | 127.3 |
| Sodium fluoride | 0.950 | 100 |
|  | 1.870 | 105.8 |
| KCN | 1.900 | 112.5 |
|  | 3.740 | 104.8 |
| PQQ | 0.01 | 147.6 |

As shown in Table 6, ethylenediamine tetraacetic acid (EDTA) strongly inhibited the enzyme activity, and 1.87 mM each of N-ethylmaleimide and monoiodoacetate partially inhibited the activity by 24 and 13%, respectively. The enzyme reaction was slightly stimulated by 5 to 27% in the presence of sodium fluoride (1.87 mM), quinine (0.95 to 1.87 mM), sodium fluoroacetate (0.95 to 1.87 mM) and $Na_2HAsO_4 \cdot 7H_2O$ (1.87 mM). The addition of 0.01 mM pyrroloquinoline quinone (PQQ) stimulated the activity by about 50%.

8) Effects of substrate concentration on reaction rate

The velocity of the oxidizing reaction with various concentrations of L-sorbosone, from 0.15 to 7.54 mM, was measured to determine the Km value for L-sorbosone. The apparent Michaelis constant was calculated to be 0.85 mM from the Lineweaver-Burk plot based on the reaction velocity when 2,6-dichlorophenolindophenol was used as the electron acceptor for the reaction.

9) Molecular weight

The molecular weight of the enzyme was measured with a gel filtration column (Sephacryl S-400 HR). The apparent molecular weight of the enzyme was calculated to be 91,000±5,000 in comparison with the molecular weight marker proteins. SDS-Polyacrylamide gel electrophoresis gave a single band with a molecular weight of 44,000±2,000.

This indicates that this enzyme is composed of two homologous subunits.

10) Purification procedure

The purification of the aldehyde dehydrogenase may, in principle, be effected by any combination of known purification methods, such as fractionation with precipitants, for example, ammonium sulfate, polyethylene glycol and the like, ion exchange chromatography, adsorption chromatography, gel-filtration chromatography, gel electrophoresis and salting out and dialysis.

As mentioned above, the aldehyde dehydrogenase provided by the present invention can be prepared by cultivating an appropriate microorganism in an aqueous nutrient medium under aerobic conditions, disrupting the cells of the microorganism and isolating and purifying the aldehyde dehydrogenase from cell-free extract of the disrupted cells of the microorganism.

The microorganisms utilized in the present invention are microorganisms belonging to the genus Gluconobacter which are capable of producing aldehyde dehydrogenase as defined hereinbefore. Functional equivalents, subcultures, mutants and variants of said microorganism can also be used in the present invention.

A preferred strain is *Gluconobacter oxydans*. The strain most preferably used in the present invention is *Gluconobacter oxydans* DSM 4025, which was deposited at the Deutsche Sammlung von Mikroorganismen in Gottingen, Germany under DSM No. 4025 on Mar. 17, 1987. The depositor was The Oriental Scientific Instruments Import and Export Corporation for Institute of Microbiology, Acedemia Sinica, 52 San-Li-He Rd., Beijing, People's Republic of China.

Moreover, a subculture of the strain was also deposited at the Fermentation Research Institute (now the National Institute of Bioscience and Human-Technology), Agency of Industrial Science and Technology, Japan, based on the stipulations of the Budapest Treaty under the deposit No. *Gluconobacter oxydans* DSM No. 4025 FERM BP-3812 on Mar. 30, 1992. The depositor was the Nippon Roche Research Center, 200 Kajiwara Aza Sotokochi, Kamakurashi, Kanagawa-ken 247, Japan.

Furthermore, European Patent Publication No. 0 278 447 discloses the characteristics of this strain.

The microorganism may be cultured in an aqueous medium supplemented with appropriate nutrients under aerobic conditions. The cultivation may be conducted at a pH of 4.0 to 9.0, preferably 6.0 to 8.0. The cultivation period varies depending on the pH, temperature and nutrient medium to be used and is preferably about 1 to 5 days. A preferred temperature range for carrying out the cultivation is from about 13° C. to about 36° C., preferably from 18° C. to 33° C.

It is usually required that the culture medium contains nutrients as assimilable carbon sources, such as glycerol, D-mannitol, D-sorbitol, erythritol, ribitol, xylitol, arabitol, inositol, dulcitol, D-ribose, D-fructose, D-glucose and sucrose, preferably D-sorbitol, D-mannitol and glycerol; and digestible nitrogen sources, such as organic substances, for example, peptone, yeast extract, baker's yeast, meat extract, casein, urea, amino acids, corn steep liquor and the like. Various inorganic substances may also be used as nitrogen sources, such as nitrates, ammonium salts and the like. Furthermore, the culture medium usually contains inorganic salts, such as magnesium sulfate, potassium phosphate, ferrous and ferric chlorides, calcium carbonate and the like.

In the following, an embodiment for isolation and purification of the aldehyde dehydrogenase from the microorganism after the cultivation is briefly described.

(1) Cells are harvested from the liquid culture broth by centrifugation or filtration.
(2) The harvested cells are washed with water, physiological saline or a buffer solution having an appropriate pH.
(3) The washed cells are suspended in the buffer solution and disrupted by means of a homogenizer, sonicator, French press or treatment with lysozyme and the like to give a solution of disrupted cells.
(4) The aldehyde dehydrogenase is isolated and purified from the cell-free extract of disrupted cells, preferably from the cytosol fraction of the microorganism.

The aldehyde dehydrogenase provided by the invention is useful as a catalyst for the production of carboxylic acids from aldehydes, especially for the production of 2-keto-L-gulonic acid from L-sorbose via L-sorbosone.

The reaction should be conducted at pH values of from about 6.0 to about 9.0 in the presence of electron acceptors, for example, 2,6-dichlorophenolindophenol, phenazine methosulfate, Wurster's blue, ferricyanide, coenzyme Q, cytochrome c and the like, in a solvent, such as, Tris-HCl buffer, phosphate buffer and the like.

A preferred temperature range for carrying out the reaction is from about 10° C. to about 50° C. When the pH and the temperature are set at about 7.0–8.0 and, respectively, 20°–40° C., the reaction usually produces the best results.

The concentration of L-sorbosone in a solvent can vary depending on other reaction conditions but, in general, is about 0.5 to 50 g/l, most preferably from about 1 to about 30 g/l.

In the reaction, the aldehyde dehydrogenase may also be used in an immobilized state with an appropriate carrier. Any means of immobilizing enzymes generally known in the art may be used. For instance, the enzyme may be bound directly to a membrane, granules or the like of a resin having one or more functional groups, or it may be bound to the resin through bridging compounds having one or more functional groups, for example, glutaraldehyde.

In addition to the above, the cultured cells are also useful for the production of carboxylic acids from aldehydes, especially for the production of 2-keto-L-gulonic acid from L-sorbosone.

The Examples which follow further illustrate the invention.

EXAMPLE 1

Preparation of aldehyde dehydrogenase

All the operations were performed at 8° C., and the buffer was 0.05M potassium phosphate (pH 7.0) unless otherwise stated.

(1) Cultivation of *Gluconobacter oxydans* DSM 4025 (FERM BP-3812)

*Gluconobacter oxydans* DSM 4025 (FERM BP-3812) was grown on an agar slant containing 5.0% D-mannitol, 0.25% $MgSO_4 \cdot 7H_2O$, 1.75% corn steep liquor, 5.0% baker's yeast, 0.5% urea, 0.5% $CaCO_3$ and 2.0% agar at 27° C. for 4 days. One loopful of the cells was inoculated into 50 ml of a seed culture medium containing 8% L-sorbose, 0.05% glycerol, 0.5% urea, 0.25% $MgSO_4 \cdot 7H_2O$, 1.75% corn steep liquor, 5.0% baker's yeast and 1.5% $CaCO_3$ in a 500 ml Erlenmeyer flask, and cultivated at 30° C. for one day on a rotary shaker (180 rpm). 10 ml each of this culture were transferred into two 500 ml Erlenmeyer flasks containing 100 ml of the same seed culture medium and cultivated in the same manner as described above. The seed culture thus prepared was used to inoculate 2 liters of medium, which contained 10% L-sorbose, 0.05% glycerol, 0.25% $MgSO_4 \cdot 7H_2O$, 3.0% corn steep liquor, 6.25% baker's yeast and 0.15% antifoam, in a 3-L jar fermentor. The fermentation parameters were 800 rpm for the agitation speed and 0.5 vvm (volume of air/volume of medium/minute) for the aeration at a temperature of 30° C. The pH was maintained at 7.0 with sodium hydroxide during the cultivation. After 40 hours of cultivation, 8 liters of the culture broth containing the cells of *Gluconobacter oxydans* DSM 4025 (FERM BP-3812) by using the 4 sets of fermentors were harvested. The slightly reddish cells were pelleted on top of the baker's yeast that was already present in the medium by centrifugation at 8,000 rpm (10,000×g), then the upper layer was removed carefully with a spatula and the cells were washed once with a 0.85% NaCl solution. As a result, 46 g of the wet weight of cells of *Gluconobacter oxydans* DSM No. 4025 (FERM BP-3812) were obtained from 8 liters of broth.

(2) Preparation of cytosol fraction

The cell paste (46 g) was suspended into 138 ml of the buffer and passed through a French pressure cell press. After centrifugation to remove intact cells, the supernatant was designated as the cell-free extract, and then the cell-free extract was centrifuged at 100,000×g for 60 minutes. The resultant supernatant (150 ml) was designated as the soluble fraction of *Gluconobacter oxydans* DSM 4025 (FERM BP-3812). After this fraction had been dialyzed against the buffer, 100 ml of the fraction having the specific activity of 1.42 units/mg protein were used for the next purification step.

(3) Diethylaminoethyl (DEAE)-cellulose column chromatography

The dialysate (100 ml) was put on a column of Diethylaminoethyl-cellulose (Whatman DE-52, 3×50 cm) equilibrated with the buffer and washed with the buffer to elute minor proteins. Then, a linear gradient of NaCl from 0.0 to 0.8M was added to the buffer. Major enzyme activity was eluted at NaCl concentrations ranging from 0.45 to 0.55M. Then, the pooled active fractions were dialyzed against the buffer.

(4) Diethylaminoethyl-Sepharose column chromatography

The dialyzed active fraction (58 ml) from the previous step was applied to a column of Diethylaminoethyl-Sepharose (Pharmacia, 1.5×50 cm) equilibrated with the buffer. After the column had been washed with the buffer containing 0.2M NaCl, a linear gradient of NaCl from 0.2 to 0.8M was added to the buffer. The enzyme activities were eluted at NaCl concentrations ranging from 0.38 to 0.42M. The fractions corresponding to aldehyde dehydrogenase activity were collected.

(5) Q-Sepharose column chromatography

The pooled active fractions (15.8 ml) from the previous step were dialyzed against the buffer and put on a column of Q-Sepharose (Pharmacia, 1.0×20 cm) equilibrated with the buffer. The column was washed with the buffer and a linear gradient of NaCl from 0.0 to 0.6M was added to the buffer.

The activities corresponding to aldehyde dehydrogenase were eluted at NaCl concentrations ranging from 0.34 to 0.37M.

A summary of the purification steps of the enzyme is shown in Table 7.

TABLE 7

Purification of dye-linked ADH from *Gluconobacter oxydans* DSM 4025

| Step | Total activity (units) | Total protein (mg) | Specific activity (units/mg-protein) | Recovery (%) |
|---|---|---|---|---|
| Soluble fraction | 1320 | 930 | 1.42 | 100 |
| DEAE-Cellulose | 427.5 | 44.5 | 9.661 | 32.4 |
| DEAE-Sepharose | 148.0 | 12.3 | 12.3 | 11.2 |
| Q-Sepharose | 81.0 | 0.825 | 98.2 | 6.14 |

(6) Purity of the isolated enzyme

The purified enzyme with a specific activity of 98.2 units per mg of protein (0.2 mg/ml) was used for the following analysis:

The molecular weight of the native aldehyde dehydrogenase was determined by high performance liquid chromatography using a size exclusion gel column (TSK gel G3000 SWXL column, 7.8×300 mm) equilibrated with 0.1M potassium phosphate buffer (pH 7.0) containing 0.3M NaCl at 254 nm and a flow rate of 1.0 ml per minute. Cyanocobalamin (1.35K), myoglobin (17K), ovalbumin (44K), g-globulin (158K) and thyroglobulin (670K) were used as molecular weight standards. The purified enzyme showed a single peak and the molecular weight was determined to be about 91,000±5,000.

In the presence of sodium dodecyl sulfate (SDS), the enzyme showed a single band with a molecular weight of about 44,000±2,000. From these results, the purified aldehyde dehydrogenase was found to consist of two homologous subunits.

(7) Identification of the reaction product

The reaction mixture containing the purified enzyme (0.02 mg), L-sorbosone (2 mg) and phenazine methosulfate (0.1 mg) in 0.5 ml of the buffer was incubated for 1.5 hours at 30° C. As a result, the product was identified to be 2-keto-L-gulonic acid in comparison with its authentic sample.

EXAMPLE 2

2-keto-L-gulonic acid production by the purified ADH

A reaction mixture containing the purified aldehyde dehydrogenase (0.04 mg protein, and prepared according to Example 1), L-sorbosone (4 mg) and phenazine methosulfate (0.2 mg) in 1.0 ml of 0.5M potassium phosphate buffer (pH 7.0) was incubated for 1.0 hour at 25° C. with gentle shaking. As a result, 2-keto-L-gulonic acid was formed at the rate of about 2.3 mg/hour.

We claim:

1. A purified aldehyde dehydrogenase having the following physico-chemical properties:
a) Molecular weight: 91,000±5,000 (consisting of two homologous subunits, each having a molecular weight of 44,000±2,000)
b) Substrate specificity: active on aldehyde compounds
c) Inhibition: by $Cu^{2+}$, $Zn^{2+}$, $Ni^{2+}$ and ethylenediamine tetraacetic acid
d) Optimum pH: 6.0–8.5
e) Optimum temperature: 20°–40° C.
f) Stimulator: $Ca^{2+}$ and pyrroloquinoline quinone.

2. The aldehyde dehydrogenase according to claim 1, which is derived from a microorganism belonging to the genus Gluconobacter which is capable of producing the aldehyde dehydrogenase having the properties:
a) Molecular weight: 91,000±5,000 (consisting of two homologous subunits, each having a molecular weight of 44,000±2,000)
b) Substrate specificity: active on aldehyde compounds
c) Inhibition: by $Cu^{2+}$, $Zn^{2+}$, $Ni^{2+}$ and ethylenediamine tetraacetic acid
d) Optimum pH: 6.0–8.5
e) Optimum temperature: 20°–40° C.
f) Stimulator: $Ca^{2+}$ and pyrroloquinoline quinone.

3. The aldehyde dehydrogenase according to claim 2, wherein the microorganism is *Gluconobacter oxydans* having the identifying characteristics of the strain *Gluconobacter oxydans* DSM No. 4025 (FERM BP-3812).

4. The aldehyde dehydrogenase according to claim 3, wherein the microorganism corresponds to *Gluconobacter oxydans* DSM No. 4025 (FERM BP-3812), or a subculture or mutant thereof belonging to the genus Gluconobacter.

5. A process for producing the aldehyde dehydrogenase having the following physico-chemical properties:
a) Molecular weight: 91,000±5,000 (consisting of two homologous subunits, each having a molecular weight of 44,000±2,000)
b) Substrate specificity: active on aldehyde compounds
c) Inhibition: by $Cu^{2+}$, $Zn^{2+}$, $Ni^{2+}$ and ethylenediamine tetraacetic acid
d) Optimum pH: 6.0–8.5
e) Optimum temperature: 20°–40° C.
f) Stimulator: $Ca^{2+}$ and pyrroloquinoline quinone,
which comprises cultivating a microorganism belonging to the genus Gluconobacter, which is capable of producing the aldehyde dehydrogenase having the above properties, in an aqueous nutrient medium under aerobic conditions, disrupting the cells of the microorganism and isolating and purifying the aldehyde dehydrogenase from the cell-free extract of the disrupted cells of the microorganism.

6. The process according to claim 5 wherein the microorganism is *Gluconobacter oxydans* having the identifying characteristics of the strain *Gluconobacter oxydans* DSM No. 4025 (FERM BP-3812).

7. The process according to claim 6, wherein the microorganism corresponds to *Gluconobacter oxydans* DSM No. 4025 (FERM BP-3812), or a subculture or mutant thereof belonging to the genus Gluconobacter.

8. A process for producing 2-keto-L-gulonic acid from L-sorbosone which comprises contacting L-sorbosone with an aldehyde dehydrogenase having the following physico-chemical properties:
a) Molecular weight: 91,000±5,000 (consisting of two homologous subunits, each having a molecular weight of 44,000±2,000)
b) Substrate specificity: active on aldehyde compounds
c) Inhibition: by $Cu^{2+}$, $Zn^{2+}$, $Ni^{2+}$ and ethylenediamine tetraacetic acid
d) Optimum pH: 6.0–8.5
e) Optimum temperature: 20°–40° C.
f) Stimulator: $Ca^{2+}$ and pyrroloquinoline quinone,
in the presence of an electron acceptor, and isolating the resulting 2-keto-L-gulonic acid from the reaction mixture.

9. A process for producing 2-keto-L-gulonic acid from L-sorbosone which comprises contacting L-sorbosone with a microorganism belonging to the genus Gluconobacter which is capable of producing the aldehyde dehydrogenase having the following physico-chemical properties:
- a) Molecular weight: 91,000±5,000 (consisting of two homologous subunits, each having a molecular weight of 44,000±2,000)
- b) Substrate specificity: active on aldehyde compounds
- c) Inhibition: by $Cu^{2+}$, $Zn^{2+}$, $Ni^{2+}$ and ethylenediamine tetraacetic acid
- d) Optimum pH: 6.0–8.5
- e) Optimum temperature: 20°–40° C.
- f) Stimulator: $Ca^{2+}$ and pyrroloquinoline quinone, in an aqueous nutrient medium under aerobic conditions, and isolating the resulting 2-keto-L-gulonic acid from the reaction mixture.

10. The process according to claim 9, wherein the microorganism is *Gluconobacter oxydans* having the identifying characteristics of the strain *Gluconobacter oxydans* DSM No. 4025 (FERM BP-3812).

11. The process according to claim 10, wherein the microorganism corresponds to *Gluconobacter oxydans* DSM No. 4025 (FERM BP-3812), or a subculture or mutant thereof belonging to the genus Gluconobacter.

12. A process for producing 2-keto-L-gulonic acid from L-sorbosone which comprises contacting L-sorbosone with a cell-free extract of a microorganism belonging to the genus Gluconobacter which is capable of producing the aldehyde dehydrogenase having the following physico-chemical properties:
- a) Molecular weight: 91,000±5,000 (consisting of two homologous subunits, each having a molecular weight of 44,000±2,000)
- b) Substrate specificity: active on aldehyde compounds
- c) Inhibition: by $Cu^{2+}$, $Zn^{2+}$, $Ni^{2+}$ and ethylenediamine tetraacetic acid
- d) Optimum pH: 6.0–8.5
- e) Optimum temperature: 20°–40° C.
- f) Stimulator: $Ca^{2+}$ and pyrroloquinoline quinone, and isolating the resulting 2-keto-L-gulonic acid from the reaction mixture.

13. The process according to claim 12, wherein the microorganism is *Gluconobacter oxydans* having the identifying characteristics of the strain *Gluconobacter oxydans* DSM No. 4025 (FERM BP-3812).

14. The process according to claim 13, wherein the microorganism corresponds to *Gluconobacter oxydans* DSM No. 4025 (FERM BP-3812), or a subcultures or mutant thereof belonging to the genus Gluconobacter.

* * * * *